United States Patent [19]

Lee et al.

[11] 4,417,063

[45] Nov. 22, 1983

[54] PROCESS FOR PREPARATION OF 6,11-DIHYDRO-11-OXODIBENZ[B,E]OX-EPINACETIC ACIDS

[75] Inventors: Thomas B. K. Lee, Whitehouse Station; George E. Lee, Somerville; Gregory M. Jobin, Bridgewater, all of N.J.

[73] Assignee: Hoechst-Roussel Pharmaceuticals Inc., Somerville, N.J.

[21] Appl. No.: 264,482

[22] Filed: May 18, 1981

[51] Int. Cl.$^3$ ............................................. C07D 313/12
[52] U.S. Cl. ......................................................... 549/354
[58] Field of Search ........................... 260/333; 549/354

[56] References Cited

U.S. PATENT DOCUMENTS

| | | | |
|---|---|---|---|
| 4,205,170 | 5/1980 | Fujimoto et al. | 549/354 |
| 4,238,620 | 12/1980 | Uno et al. | 549/354 |
| 4,263,437 | 4/1981 | Fujimoto et al. | 549/354 |

OTHER PUBLICATIONS

A. Merz, Synthesis, vol. 10, pp. 724–725 (Oct. 1974).
P. Kuhl et al., Synthesis, pp. 825–826 (Dec. 1976).
J. Org. Chem., 33, 2565–2566 (1968).
Morrison and Boyd, Organic Chemistry, 3rd Ed. 637 (1973).
Berichte, 96, 1524 (1963).
Organic Synthesis, Coll. vol. 1, John Wiley & Sons N.Y. (1932) p. 224–225.
Proc. Soc. Exptl. Biol. Med., III, 544–547 (1962).
J. Pharmacol. Exp. Ther., 141, 369–376 (1963).
Proc. Soc. Exptl. Biol. Med., 95, 729–731 (1957).
J. Med. Chem., 21, 633–639 (1978).
Paul N. Rylander, Catalytic Hydrogenation over Platinum Metals, Academic Press (1967) New York, Chapters 15, 24 and 25, pp. 405–429.
Walter H. Hartung et al., Organic Reactions, vol. 7, John Wiley & Sons, Inc. New York, Chapter 5.
Weinstock et al., Tetrahedron Letters No. 46 (1975) pp. 3979–3982.
V. Kohli et al., Tetrahedron Letters, vol. 21 (1980) pp. 501–502.

Primary Examiner—Norma S. Milestone

[57] ABSTRACT

A method for the preparation of 6,11-dihydro-11-oxodibenz[b,e]oxepin-acetic acids having pharmaceutical activity is disclosed. Compounds represented by the formula:

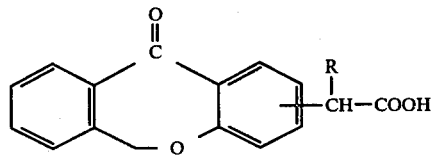

wherein R is OH or Cl are provided as intermediates. An aldehyde of the formula:

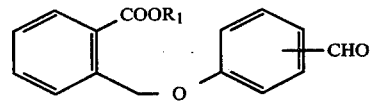

wherein $R_1$ is a lower alkyl, e.g., 1 to 4 carbon atoms, is reacted with chloroform and aqueous base to form an α-hydroxy dicarboxylic acid. Alternatively, the aldehyde can be converted to the corresponding cyanohydrin, which is then converted to the corresponding α-hydroxy dicarboxylic acid. The α-hydroxy dicarboxylic acid can also be prepared from reaction of a halogenated toluate of the formula:

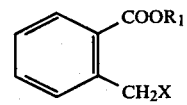

wherein X is Cl or Br with mandelic acid or a derivative thereof of the formula:

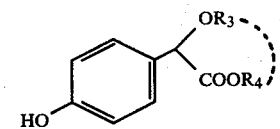

wherein $R_3$ and $R_4$ are independently selected from hydrogen and alkyl of 1 to 4 carbon atoms. The α-hydroxy dicarboxylic acid is cyclized and then converted to the oxepin acetic acid by reduction. Alternatively, the α-hydroxy dicarboxylic acid is cyclized and converted to an α-chloro-substituted oxepin acetic acid, which is then converted to the unsubstituted oxepin acetic acid by reductive removal of chlorine.

10 Claims, No Drawings

PROCESS FOR PREPARATION OF 6,11-DIHYDRO-11-OXODIBENZ[B,E]OXEPINA-CETIC ACIDS

BACKGROUND OF THE INVENTION

The present invention relates to new processes for the preparation of 6,11-dihydro-11-oxodibenz[b,e]oxepin-2-acetic acid and the corresponding 3-isomer. 6,11-Dihydro-11-oxodibenz[b,e]oxepin-acetic acids produced by the processes of the invention can be represented by the formula:

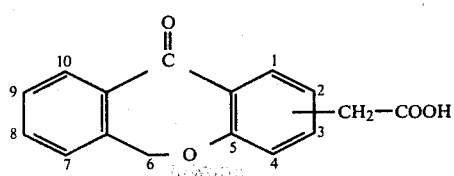

in which the $CH_2$-COOH moiety is in the 2- or 3-position. These compounds are known to exhibit antiinflammatory and analgesic activity. Processes of this invention also produce certain intermediate or precursor compounds, which are novel and are useful for the production of the 6,11-dihydro-11-oxodibenz[b,e]oxepinacetic acids. Of particular interest are the processes as they relate to the preparation of 6,11-dihydro-11-oxodibenz[b,e]oxepin-2-acetic acid.

SUMMARY OF THE INVENTION

Novel intermediate or precursor compounds that can be prepared in accordance with the invention are isomers of the following formulae:

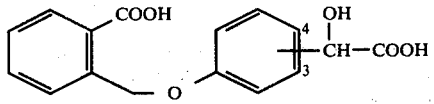

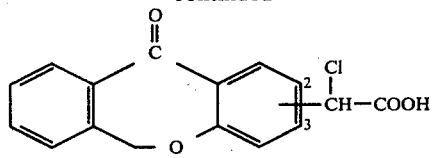

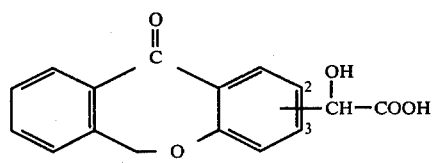

These isomers are obtainable by following the processes of the invention described below.

Another aspect of the invention relates to a novel aldehyde starting material of the formula:

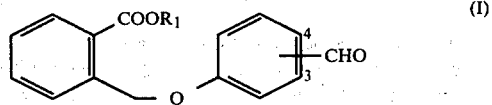

where $R_1$ is alkyl having 1 to 4 carbon atoms and where the -CHO group is in the 3- or 4-position. This invention also provides a novel cyanohydrin intermediate of the formula:

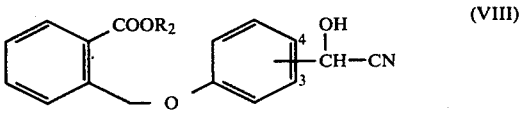

wherein $R_2$ is hydrogen or alkyl from 1 to 4 carbon atoms and the cyanohydrin group is in the 3- or 4-position.

In accordance with the novel process of the present invention, 6,11-dihydro-11-oxodibenz[b,e]oxepin-acetic acid compounds can be prepared by a direct reaction beginning with an aldehyde compound of formula (I), which is reacted with chloroform and aqueous hydroxide solution in the presence of a phase transfer catalyst followed by cyclization and reduction in accordance with the following reaction sequence:

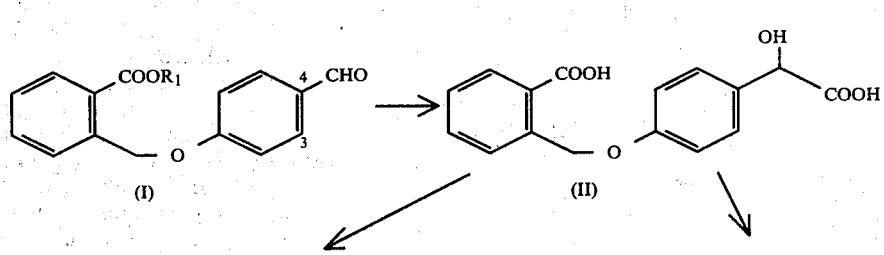

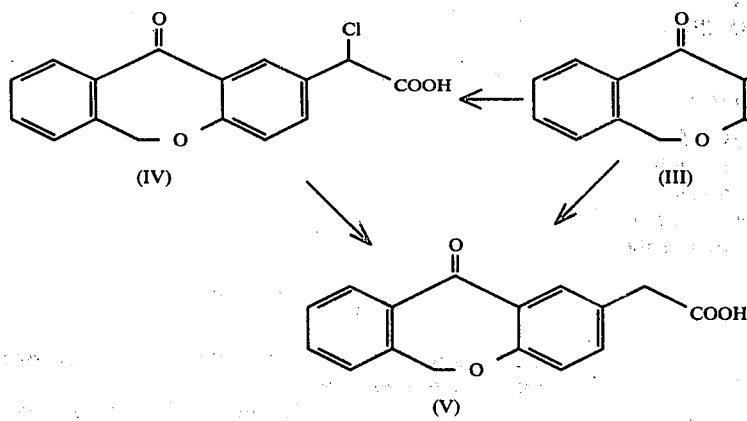
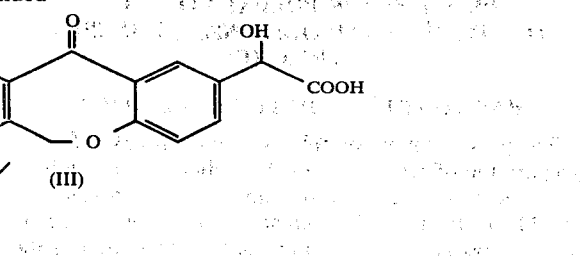

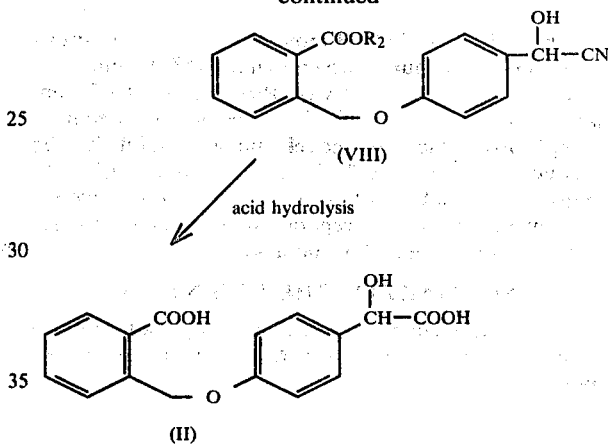

where $R_1$ is as defined above. The corresponding 3-isomer of compound (V) can be prepared by utilizing compound (I) with the -CHO moiety in the 3-position instead of the 4-position as shown above.

A still further embodiment of the invention involves the formation of compound (II) by the reaction sequence:

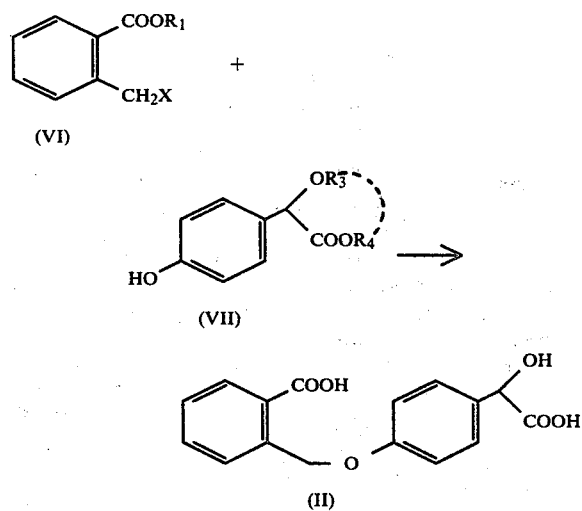

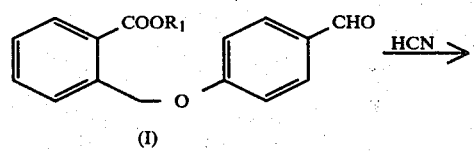

where $R_1$ is as defined above, $R_3$ and $R_4$ are independently selected from H and alkyl having 1 to 4 carbon atoms and X is chlorine or bromine. In another embodiment, $R_3$ and $R_4$ together form a hetero ring system as depicted by the dotted lines.

In another embodiment of the invention, the aldehyde (I) is converted to a cyanohydrin (VIII) by reaction with HCN, and the cyanohydrin is converted to the hydroxy acid (II) by means of acid hydrolysis as follows:

Generally, the reaction sequences illustrated above in the reaction diagram may be carried out in the following manner.

DETAILED DESCRIPTION

An aldehyde (I) can be prepared using conventional techniques. For example, an ester of α-bromo-o-toluic acid can be formed by esterifying toluic acid with a lower alkanol followed by bromination with N-bromosuccinimide. The resulting lower alkyl α-bromo-o-toluic acid ester can then be reacted with commercially available p-hydroxybenzaldehyde in a solvent using a Williamson ether synthesis to form aldehyde (I). Typical of suitable solvents are polar organic solvents, such as butanone, dimethylformamide, alcohols and acetonitrile. The Williamson synthesis can be carried out at about 50° to about 150° C.

Aldehyde (I) with a lower alkyl ester group, i.e., an ester with 1 to 4 carbon atoms in the alcoholic unit, is allowed to react with chloroform and a suitable base and preferably in the presence of a phase transfer catalyst. Representative bases are NaOH, KOH, LiOH and the like. Chloroform together with NaOH have been found to give particularly good results. Suitable for use as the catalyst are the tetraalkylammonium salts, such as the halides including methyltriethylammonium chloride, methyltrialkylammonium chloride where the alkyl groups contain about 8 to about 10 carbon atoms, methyltricaproyl ammonium chloride, as well as aromatic containing ammonium salts, such as benzyltriethyl ammonium chloride. Phase transfer catalysts are known in the art and any suitable one may be employed for purposes of this invention, such as Adogen 464 and Aliquat 336. As the reaction to form the diacid (II) is an exothermic reaction, the temperature may be controlled between 10° C. and up to or close to the reflux temperature of the solvent employed in the reaction. It is desirable to hold the reaction mixture for a period of about ½ hour up to about 5 hours for suitable aging to insure that hydrolysis is complete. The reaction is carried out at about atmospheric pressure. After the reaction is completed, the aqueous and organic layers are separated, and the product (II) may be recovered from the aqueous phase by conventional means, such as acidification, extraction with ethyl acetate or the like. Phase transfer catalyzed formation of α-hydroxy carboxylic acids from aromatic aldehydes is described by A. Mir in *SYNTHESIS* Vol. 10, pp. 724–725 (October 1974).

The α-hydroxy dicarboxylic acid (II) obtained by the foregoing reaction can then be converted to its trichloro intermediate and cyclized by a Friedel Crafts reaction to form the acid substituted by chlorine on the α-carbon atom (IV). Conversion of II to its trichloro intermediate may be carried out by treatment with thionyl chloride in a solvent, particularly halogenated solvents, such as dichloromethane, dichloroethane and the like, at a temperature ranging from about room temperature to about 85° C. At least about 3 equivalents, preferably about 3 to about 5 equivalents, of thionyl chloride are used for this reaction. When operating at room temperature, the period of time can vary from about 3 hours to about 16 hours to provide for adequate aging. At higher temperature, less aging time is required. A catalyst, such as dimethyl formamide, to speed the formation of acid chloride may be employed if desired.

For the Friedel Crafts reaction to form the chloro-substituted acid, the reaction mixture is cooled to about 5° to about 15° C., and the usual Friedel Crafts catalyst, $AlCl_3$, is added, making certain the temperature does not rise above about 20° C. The reaction mixture is then stirred for about 1 to about 5 hours, and ice cold water is slowly added to effect hydrolysis while maintaining the temperature of the mixture to less than about 15° C. The product is obtained from the organic layer after separation of the aqueous 6,11-dihydro-α-chloro-11-oxodibenz[b,e]oxepin-acetic acid (IV). It has been found important to avoid the presence of aqueous base during the work-up following reaction.

The conversion of compound (IV) to the corresponding 6,11-dihydro-11-oxodibenz[b,e]oxepin-acetic acid final product (V) involves reductive removal of chlorine from the α-carbon atom. Selective reduction occurs at the α-carbon atom rather than the potentially reductively labile 6- and 11-positions of the tricyclic nucleus, and it has surprisingly been found that cleavage of the tricyclic nucleus does not accompany chlorine removal. Reaction conditions for this reaction are generally mild. For example, the reduction reaction may take place using hydrogen in the presence of a catalyst, such as a catalytic amount of palladium on carbon. Typically, the catalyst will have about 1 to about 5 weight percent palladium on carbon and will be employed in an amount of about 5 to about 100, preferably about 5 to about 10, weight percent of reactants. A less active catalyst could be used. The use of hydrogen in amounts that would lead to over-reduction of compound (IV) should be avoided. The reduction reaction is generally carried out in the presence of a suitable solvent, such as ethyl acetate, at about a neutral pH. The use of solvents that may be hydrogenated should be avoided. It has been found that the presence of a material capable of removing or absorbing hydrogen chloride is important in the system. Molecular sieves, such as sodium aluminosilicates, in an effective amount, are preferred for this purpose. Typically, these materials are identified in terms of their average pore size expressed in Angstroms, and a material with the identification of 4 Angstroms has been found to be useful for purposes of the invention. The amount employed will depend upon pore size, surface area and reaction conditions, but preferably should be sufficient to scavenge substantially all of the HCl formed. In this reduction reaction, one equivalent of hydrogen is consumed. The pressure of the hydrogen can range from about 1 atmosphere to about 10 psi. Elevated temperatures are preferably avoided.

As an alternative reduction method for converting compound (IV) to the unsubstituted acetic acid (V), an organotin hydride, such as tributyl tin hydride, can be used in the foregoing reaction with standard reaction conditions being employed. Generally, atmospheric pressure is used for the reduction reaction. Use of a catalyst, such as 2,2'-azobis-2-methyl propionitrile, to accelerate the reaction is optional. Solvents, such as toluene and benzene, containing tetrahydrofuran to solubilize the acid, can be employed.

An alternative procedure involves the reaction of the dicarboxylic acid (II) to form the corresponding cyclized α-hydroxy monocarboxylic acid (III). The cyclization reaction is carried out using thionyl chloride in an amount of about 3 equivalents to form the intermediate trichloro compound, followed by a Friedel Crafts reaction using about 1 to about 2 equivalents of aluminum trichloride. Following reaction aqueous alkaline medium, such as sodium hydroxide or sodium bicarbonate, is employed in the work up in order to obtain the α-hydroxy compound, III.

It is also possible to proceed from the cyclized α-hydroxy monocarboxylic acid compound (III) to the cyclized α-chloro-substituted acid (IV). This can be carried out by reacting the hydroxy containing compound (III) with about two to about three equivalents of thionyl chloride in the presence of a halogenated solvent, such as dichloromethane, dichloroethane or the like. Methylene chloride is preferred. Generally, the temperature of the reaction can range from about room temperature to the reflux temperature of the solvent. The reaction time can vary over a period of about 2 to about 16 hours. In the formation of the cyclized α-chloro-substituted acid (IV), it is desirable to avoid contact with an aqueous base, such as an aqueous solution of sodium hydroxide or sodium carbonate, during the work up.

Another alternative method of forming the 6,11-dihydro-11-oxodibenz[b,e]oxepin acetic acid (V) is to convert the cyclized hydroxy acid compound (III) directly into the desired acetic acid final product. This can be carried out using hydrogen and a catalyst, or stannous chloride, or a red phosphorus-acetic acid mixture and a suitable solvent.

In an alternative embodiment of the invention, the α-hydroxy dicarboxylic acid (II) may be obtained by utilizing as the starting material a cyanohydrin (VIII), which is derived from the initial aldehyde compound (I) by reaction with HCN. Addition of HCN to a carbonyl group is a well-known reaction as shown, for example, by Morrison and Boyd, ORGANIC CHEMISTRY, 3rd Ed., p. 637, and Berichte 96, p. 1524 (1963). When using the cyanohydrin (VIII) as an intermediate to form the α-hydroxy dicarboxylic acid (II), generally the reaction is carried out in the presence of a solvent. Conversion of the cyanohydrin group into a carboxylic acid group is shown, for example, in Berichte 96, p. 1524 (1963).

As previously described, mandelic acid or a derivative thereof can be reacted with an α-bromo or α-chloro substituted o-toluic acid ester to form the α-hydroxy acid (II). In the formula for compound (VII), $R_1$ and $R_2$ are independently selected from hydrogen or $C_1$ to $C_4$ alkyl and together can form a hetero ring system. For this reaction to take place, typically para-hydroxymandelic acid (VII wherein $R_1$ and $R_2$ are hydrogen) is first converted to the corresponding ester by treatment with a $C_1$ to $C_4$ alkanol in the presence of sulfuric acid or an ion-exchange medium. Referring to formula (VII), the resulting product would be the corresponding lower alkyl ester wherein $R_1$ is hydrogen and $R_2$ is a $C_1$ to $C_4$ alkyl group. This ester in the presence of an alkaline material, such as $K_2CO_3$, and a polar solvent, such as 2-butanone, will react with the lower alkyl ester of a substituted α-halo-o-toluic acid (VI) to produce the uncyclized α-hydroxy dicarboxylic acid (II) after basic hydrolysis. Preferred for this purpose are the methyl and ethyl esters of α-bromotoluic acid.

As is well known to those skilled in the art, the reaction times indicated in the foregoing discussion are correlated to the reaction temperature so that shorter times are generally possible when using higher temperatures.

6,11-dihydro-11-oxodibenz[b,e]oxepin-acetic acid compounds (V) produced by the methods of the present invention are useful as antiinflammatory agents due to their ability to suppress inflammation in mammals. The activity of the compounds is demonstrated in the carrageenan induced rat paw edema antiinflammatory assay [Proc. Soc. Exptl. Biol. Med., III 544 (1962); J. Pharmacol. Exp. Ther., 141, 369 (1963)].

In addition, the 6,11-dihydro-11-oxodibenz[b,e]oxepin-acetic acid compounds (V) produced by the process of the present invention are useful as analgesic agents due to their ability to alleviate pain in mammals. The activity of the compounds is demonstrated in the 2-phenyl-1,4-benzoquinone-induced writhing test in mice, a standard assay for analgesia [Proc. Soc. Exptl. Biol. Med., 95, 729 (1957)].

The intermediate and precursor compounds identified above by the structural formulae (I), (II), (III), (IV) and (VIII) are useful because they can be utilized to form the final acetic acid products, which in turn are valuable as pharmaceutical and veterinary products.

The following examples are intended to illustrate the process of the invention. All percentages are by weight unless otherwise indicated.

EXAMPLE 1

Formation of Ethyl 2-[4-(formyl)phenoxymethyl]benzoate (I)

A mixture of

| | |
|---|---|
| ethyl α-bromo-o-toluate | 48.6 g (0.2 moles) |
| p-hydroxy benzaldehyde | 25.6 g (0.21 moles) |
| $K_2CO_3$ | 123 g (0.88 moles) |
| 2-butanone and | 800 ml |
| NaI | 2.2 g | was refluxed for 18 hours. The reaction mixture was cooled to room temperature, filtered and washed with 100 ml 2-butanone. The filtrate was concentrated by distillation under reduced pressure. The residue was treated with 350 ml ethyl ether and washed twice with 150 ml of 5% sodium hydroxide solution and then washed one time with 150 ml of a 5% sodium chloride solution. It was then dried with $MgSO_4$, filtered and the ether was removed by distillation under reduced pressure to yield the crude product, which was triturated with 300 ml hexane. After filtration and drying, 29.7 grams of purified product having a melting point of 60° C.–62° C. was obtained. IR and proton-NMR analyses agreed with the structure for ethyl 2-[4-(formyl)-phenoxymethyl]benzoate, i.e.:

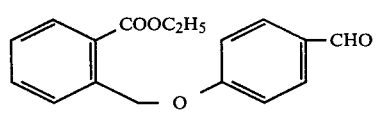

(I)

EXAMPLE 2

Formation of 4-(2-carboxybenzyloxy)-α-hydroxy-phenyl acetic acid (II)

A solution of 2.8 grams of ethyl 2-[4-(formyl)phenoxymethyl]benzoate (I) was added dropwise to a stirred mixture containing 0.11 grams of benzyl triethylammonium chloride, a phase transfer catalyst, in 2 ml chloroform and 2.5 ml of 50% NaOH at approximately 50°–60° C. The mixture was aged at that temperature for one half hour and then at room temperature for one half hour. The reaction was quenched into 15 ml water and 15 ml $CH_2Cl_2$. The layers were separated and acidified with concentrated HCl and then extracted twice with 20 ml ethyl acetate. The combined ethyl acetate extract was washed three times with 20 ml of water, dried with $Na_2SO_4$, filtered and then concentrated in vacuo to yield 1.3 grams of a yellow solid. IR and proton-NMR analyses showed this to be 4-(2-carboxybenzyloxy)-α-hydroxy-phenyl acetic acid and a small amount of (I).

EXAMPLE 3

Formation of 6,11-dihydro-α-hydroxy-11-oxodibenz[b,e]oxepin-2-acetic acid (III) by Cyclization of α-hydroxy Diacid (II)

In a 25 flask were charged 1 gram of 4-(2-carboxybenzyloxy)-α-hydroxy-phenyl acetic acid, 5 ml dichloromethane and 0.77 ml (3.2 equiv.) thionyl chloride with 1 drop dimethylformamide (DMF). These ingredients were heated together to the reflux temperature of the solvent for 5 hours. Thereafter, the reaction mixture was cooled to room temperature and aged for 16 hours. The reaction was then cooled to 10° C., and 0.53 grams (1.2 equiv.) aluminum trichloride ($AlCl_3$) was added over a period of 20 minutes keeping the temperature under 20° C. These components were stirred for two hours, and then 10 ml ice cold water was added slowly while keeping the temperature below 15° C. The layers were then separated, and the aqueous layer was extracted with 5 ml dichloromethane. The dichloromethane fractions were combined and then removed by distillation under reduced pressure. The residue was treated with 20 ml of 15% sodium hydroxide solution and then acidified with about 6 concentrated hydrochloric acid until the pH was acidic. A precipitate that formed was dried in an oven at 70° C. for 16 hours to yield 0.6 grams of a dark solid representing a 57% yield of 6,11-dihydro-α-hydroxy-11-oxodibenz [b,e]oxepin-2-acetic acid.

EXAMPLE 4

Formation of 6,11-dihydro-α-chloro-11-oxodibenz[b,e]oxepin-2-acetic acid (IV) from Cyclized Hydroxy Acid (III)

A mixture containing 0.2 grams of 6,11-dihydro-α-hydroxy-11-oxodibenz[b,e]oxepin-2-acetic acid (II), 0.149 grams (2 equiv.) of thionyl chloride and 5 ml of 1,2-dichloroethane was refluxed for 6 hours. The reaction was quenched by the addition of 10 ml of water, and the water was back extracted with 5 ml of dichloroethane. The combined organic fraction was basified with 5 ml 20% sodium hydroxide. The aqueous layer was separated and the mixture was promptly acidified with 3 N HCl until a pH of less than 2 was obtained. It was then extracted with 15 ml dichloromethane. The organic fraction was concentrated to yield an oil. Mass spectrum and proton-NMR showed 6,11-dihdyro-α-chloro-11-oxodibenz[b,e]oxepin-2-acetic acid was obtained.

EXAMPLE 5

Direct Production of 6,11-dihydro-α-chloro-11-oxodibenz[b,e]oxepin-2-acetic acid (IV) from α-Hydroxy Diacid (II)

A mixture containing
   9.5 grams of 4-(2-carboxybenzyloxy)-α-hydroxyphenyl-acetic acid (II),
   11.97 grams (3.2 equiv.) thionyl chloride,
   45 ml dichloromethane, and
   dimethylformamide, 4 drops
was refluxed for several hours and then cooled to 10° C. Aluminum chloride (5.02 grams, 1.2 equivalents) was added maintaining the temperature under 20° C. After stirring for 2 hours at that temperature, cold water was added slowly keeping the temperature below 15° C. The layers were separated, and the aqueous layer was extracted with 20 ml dichloromethane. The organic layers were combined and washed with 20 ml ammonium chloride and concentrated to provide an oil. This oil was dissolved in 17 ml acetonitrile and 8 ml 6 N HCl and then refluxed for one hour. This mixture was then cooled to room temperature and aged for 16 hours. A slight precipitate that formed was filtered. The mother liquor was concentrated to yield the crude product as an oil in the amount of 8.15 grams. Purification by preparative HPLC (5% acetic acid/toluene) provided 1.29 grams of 6,11-dihydro-α-chloro-11-oxodibenz[b,e]oxepin-2-acetic acid.

EXAMPLE 6

Reduction of Cyclized α-chloro Compound (IV) to Acetic Acid Product (V) with Pd/C A mixture containing 6,11-dihydro-α-chloro-11-oxodibenz[b,e]oxepin-2-acetic acid in the amount of 0.2 grams, 0.2 grams of 5% palladium-carbon reduction catalyst, 30 ml ethyl acetate and commercially available 4Å molecular sieve (Davidson Grade 514, Type 4A, 8-12 mesh beads, alumina silicate base with sodium cation, available from W. R. Grace) was treated with hydrogen (10 psi). The reduction reaction was run for 4 hours and then worked up by filtration and concentration in vacuo to yield 0.18 grams of crude product. 6,11-dihydro-11-oxodibenz[b,e]oxepin-2-acetic acid (V) was obtained after purification by chromatography on silica gel using ethyl acetate. Its structure was confirmed by comparison of its infra-red, proton-NMR and thin layer chromatography with that of an authentic sample.

EXAMPLE 7

Reduction of Cyclized α-chloro Compound (IV) to Acetic Acid Product (V) with Tributyl Tin Hydride A mixture containing
   0.303 g of 6,11-dihydro-α-chloro-11-oxodibenz[b,e]oxepin-2-acetic acid (1.0 mmol) (IV),
   0.320 g of tributyl tin hydride (1.1 mmol),
   0.164 g of 2,2'-azobis-2-methyl propionitrile (10 mmol),
   3 ml of tetrahydrofuran, and
   3 ml of toluene
was heated at reflux temperature for 2 hours after which a second equivalent (1.1 mmol) of tributyl tin hydride was added to the vessel. After 2 more hours at reflux temperature, the reaction mixture was removed from the vessel, concentrated in vacuo and partitioned between acetonitrile/hexane (5 ml/5 ml). The resulting heterogeneous acetonitrile layer was dissolved in about 5 ml tetrahydrofuran to form a homogeneous phase, which was concentrated in vacuo and eluted through silica gel, using ethyl acetate/methanol/ether (1:1:1 volume ratio) to give about 0.35 g of a light brown oil containing 6,11-dihydro-11-oxodibenz[b,e]oxepin-2-acetic acid (V).

What is claimed is:

1. A process for the preparation of a compound having the formula

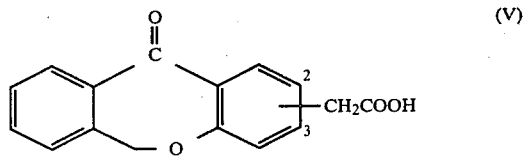

(V)

wherein the -CH₂COOH moiety is in the 2- or 3-position, said process comprising reacting a compound of the formula

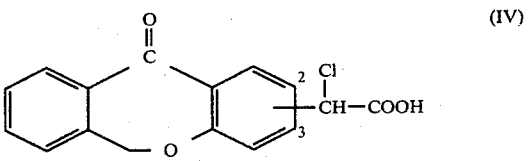

(IV)

in solution in an organic solvent with at least one equivalent of hydrogen as a reducing agent, in the presence of a palladium on carbon catalyst and a sufficient amount of a molecular sieve capable of scavenging HCl formed during reaction.

2. Process according to claim 1 wherein the catalyst is employed in an amount of about 5 to about 100 weight percent of reactants.

3. Process according to claim 2 wherein the catalyst contains about 1 to about 5 weight percent palladium on carbon.

4. Process according to claim 3 wherein the catalyst is employed in an amount of about 5 to about 10 weight percent of reactants.

5. Process according to claim 4 wherein said palladium on carbon catalyst is in an amount of about 5 percent by weight of reactants, said solvent is ethyl acetate, said molecular sieve is a sodium aluminosilicate and reaction is carried out at a pH of about 7.

6. A process for the preparation of 6,11-dihydro-11-oxodibenz[b,e]oxepin-2-acetic acid, said process comprising reacting 6,11-dihydro-α-chloro-11-oxodibenz[b,e]oxepin-2-acetic acid in solution in an organic solvent with at least one equivalent of hydrogen as a reducing agent, in the presence of a palladium on carbon catalyst and a sufficient amount of a molecular sieve capable of scavenging HCl formed during reaction.

7. Process according to claim 6 wherein the catalyst is employed in an amount of about 5 to about 100 weight percent of reactants.

8. Process according to claim 7 wherein the catalyst contains about 1 to about 5 weight percent palladium on carbon.

9. A process according to claim 8 wherein said palladium on carbon catalyst is in an amount of about 5 to about 10 percent by weight of reactants.

10. A process according to claim 9 wherein said palladium on carbon catalyst is in an amount of about 5 percent by weight of reactants, said solvent is ethyl acetate, said molecular sieve is a sodium aluminosilicate and reaction is carried out at a pH of about 7.

* * * * *